United States Patent [19]

Clark et al.

[11] Patent Number: 5,674,667
[45] Date of Patent: Oct. 7, 1997

[54] PHOTOGRAPHIC ELEMENT CONTAINING PYRROLOYLACETAMIDE YELLOW COUPLER

[75] Inventors: Bernard Arthur Clark, Maidenhead; Hamish McNab, Edinburgh; Craig Cameron Sommerville, Spean Bridge, all of United Kingdom

[73] Assignee: Eastman Kodak Company, Rochester, N.Y.

[21] Appl. No.: 669,192

[22] Filed: Jun. 24, 1996

[30] Foreign Application Priority Data

Jun. 28, 1995 [GB] United Kingdom .................. 9513114

[51] Int. Cl.$^6$ ..................................... G03C 7/36
[52] U.S. Cl. .................. 430/388; 430/389; 430/556; 430/557
[58] Field of Search ................... 430/556, 557, 430/388, 389

[56] References Cited

U.S. PATENT DOCUMENTS 5,066,576  11/1991  Ichijima et al. ................. 430/557

*Primary Examiner*—Lee C. Wright
*Attorney, Agent, or Firm*—Arthur E. Kluegel

[57] ABSTRACT

The present invention provides a photographic element comprising a silver halide emulsion layer having associated therewith a dye-forming coupler of formula (I):

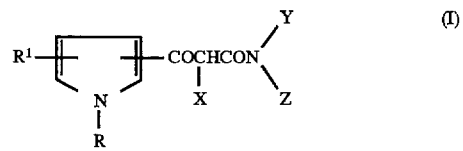

wherein X is H or a coupling-off group, R and $R^1$ are independently selected from H and substituent groups; Y and Z are independently selected from H and alkyl, aryl or heteroaryl groups; provided that Y and Z taken together with the nitrogen atom may form a 5–10 membered heterocyclic ring group which may contain one or more further heteroatoms selected from N, O and S.

14 Claims, No Drawings

PHOTOGRAPHIC ELEMENT CONTAINING PYRROLOYLACETAMIDE YELLOW COUPLER

FIELD OF THE INVENTION

The present invention relates to photographic elements containing silver halide based photographic emulsions having associated therewith pyrroloylacetamide yellow image-dye-forming couplers.

BACKGROUND OF THE INVENTION

Photographic layers sensitive to blue light for use in a color photographic material typically contain a yellow coupler which, on reaction with an oxidized p-phenylenediamine developer, forms a yellow dye. Most commercially available photographic films contain pivaloyl- or benzoyl- acetanilide yellow couplers. These classes of couplers are, in general, satisfactory, but it would be desirable to have available other types of couplers which might present a different combination of properties, for example, contrast on the one hand and dye stability on the other. Dodecyl 4-chloro-3-[2-(1-benzyl-5-ethoxy-2,4-dioxo-imidazolidin-3-yl)-2-(2,2-dimethylpropanoyl) acetamido] benzoate, for example, has good dye stability, but has a relatively poor contrast; dodecyl 4-chloro-3-[2-(1-benzyl-5-ethoxy-2,4-dioxo-imidazolidin-3-yl)-2-(4-methoxybenzoyl) acetamido] benzoate, on the other hand, has a relatively good contrast but has poor dye stability.

It is therefore a problem to be solved to provide a new class of yellow couplers that present the possibility of an improved combination of photographic properties when incorporated in a photographic element.

SUMMARY OF THE INVENTION

The invention provides a photographic element comprising a silver halide emulsion layer having associated therewith a dye-forming coupler of formula (I):

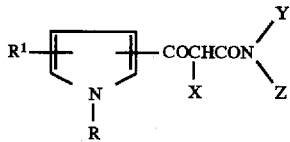

wherein X is H or a coupling-off group, R and $R^1$ are independently selected from H and substituent groups; Y and Z are independently selected from H and alkyl, aryl or heteroaryl groups; provided that Y and Z taken together with the nitrogen atom may form a 5–10 membered heterocyclic ring group which may contain one or more further heteroatoms selected from N, O and S.

The invention provides yellow dye-forming couplers having a chemical formula not previously discovered useful for this purpose.

DETAILED DESCRIPTION OF THE INVENTION

In a preferred aspect of the present invention there is provided a yellow coupler of formula (II):

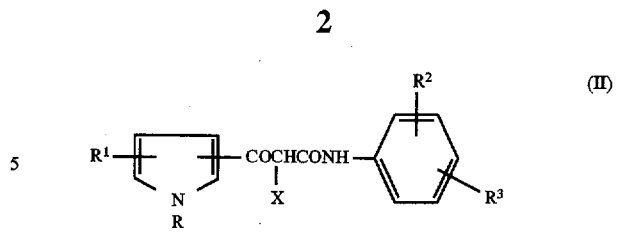

wherein X is H or a coupling-off group; and R, $R^1$, $R^2$, and $R^3$, independently, are selected from H and coupler-modifying functional groups.

Said coupling-off group is a group adapted to split-off from the coupler as a result of the reaction between the coupler and the oxidation product of an arylamine color developer. A coupler-modifying functional group is any substituent which by its presence in the coupler structure influences the photographic or physical properties of a coupler or the dye derived from the coupler.

The present invention also includes a photographic element containing a pyrroloylacetamide compound of formula (I) as an image-dye-forming coupler, in association with a light sensitive silver halide emulsion layer.

In yet another aspect the present invention provides a multi-color photographic material comprising a support bearing yellow, magenta and cyan image-dye-forming units comprising at least one blue-, green- or red-sensitive silver halide emulsion layer having associated therewith at least one yellow, magenta or cyan dye-forming coupler respectively, wherein at least one dye-forming coupler, suitably associated with a blue sensitive layer, is a pyrroloylacetamide coupler in accordance with the present invention.

Preferably, the yellow coupler may be a pyrrol-2-oylacetanilide of formula (III):

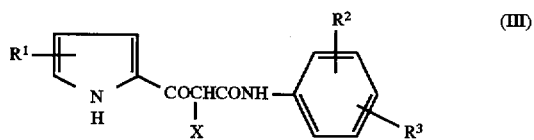

It will be appreciated however that in its broadest aspect, the present invention also embraces pyrrol-3-oylacetanilides of formula (IV):

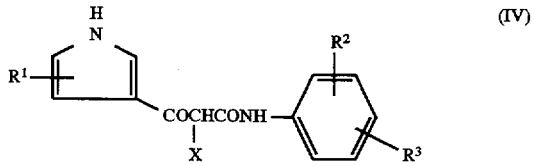

Typically, R, $R^1$, $R^2$, and $R^3$ may be selected, independently, from H, coupler-solubilising groups, ballasting groups and dye hue-modifying groups.

R may be H, unsubstituted or substituted alkyl, aryl or heteroaryl. Typically R may be selected from lower (C1–C8) alkyl, phenyl or pyridinyl groups. As defined herein the term lower alkyl refers to a straight or branched chain alkyl group having from 1 to 8 carbon atoms.

In some preferred embodiments of the invention, the coupler may be a pyrrol-2-oyl species, and R may be methyl or phenyl.

$R^1$, $R^2$, and $R^3$ may be selected from H, halogen, alkyl, aryl, heteroaryl, carboxylic acid, alkoxycarbonyl, aryloxycarbonyl, primary or secondary alkyl- or aryl-amido, alkyl- or aryl- sulfonamido, primary, secondary or tertiary amino, alkoxy, aryloxy, acyloxy, alkyl- or aryl-carbamoyl, alkyl- or aryl- sulfamoyl, alkyl- or aryl- sulfonyl and alkyl- or aryl- sulfonyloxy groups. In one aspect of the present invention, at least one of $R^1$, $R^2$, and $R^3$ may contain at least six carbon atoms.

Any of the above substituents of R, $R^1$, $R^2$, and $R^3$ other than H and halogen, may be substituted with one or more of the same or different substituents of $R^1$, $R^2$, and $R^3$ as hereinabove defined.

Typically, $R^1$ may be selected from H, halogen, alkyl, alkoxy, alkylsulfonyloxy, alkylsulfonamido and alkoxycarbonyl.

In one embodiment, $R^1$ may be H. In another embodiment, the coupler may be a pyrrol-2-oyl-acetanilide of formula (III) and $R^1$ may be methoxy; alternatively $R_1$ may be methyl, chloro, hexadecylsulfonyloxy, N-hexadecylsulfonamido or dodecyloxycarbonyl. Typically, $R^2$ may be a halogen, alkoxy or trifluoro-methyl. In one embodiment, $R^2$ may be orthochloro. In a different aspect of the invention, $R^2$ may be ortho-methoxy.

In one aspect of the present invention, $R^3$ may be a coupler-solubilising or coupler-ballasting functional group. Typically, $R^3$ may be a carboxyester. In one embodiment, $R^3$ may be dodecyloxycarbonyl or hexadecyloxycarbonyl. Alternatively, $R^3$ may be an alkyl sulfonamide such as, for example, N-dodecylsulfonamide or N-hexadecylsulfonamide.

In a different aspect of the invention, $R^3$ may be an N-amidophenylether such as, for example, 3-(2,4-di-tert-pentylphenoxy)butanoylamino. In a further aspect of the invention, $R^3$ may be an alkylsulfonyloxy, such as, for example, hexadecyl-sulfonyloxy. In yet a further aspect $R^3$ may be an alkylamino-sulfonyl, such as, for example, dodecylaminosulfonyl.

It will be appreciated that X may be H or any coupling-off group known to a person skilled in the art. In some embodiments, X may be selected from halogen, acyloxy, sulfonyloxy, aryloxy, heteroaryloxy, arylthio, heteroarylthio, urethane, imido, 2,4-oxazolidinedione, pyridone, pyridazone, phthalimido, succinimido, hydantoinyl, triazole, triazoledione, tetrazole, imidazole, pyrazole and benzotriazole. Any of the above substituents, other than H and halogen, may be substituted with one or more substituents $R_1$, $R_2$ and $R_3$ as hereinbefore defined. In some embodiments, X may be chloro. Alternatively, X may be hydantoinyl substituted with benzyl, alkoxy or alkyl, preferably 1-benzyl-5-ethoxyhydantoin-3-yl. In some embodiments, X may be phenoxy substituted with alkylsulfonyl or arylsulfonyl, preferably p-methylsulfonylphenoxy, p-benzyloxyphenylsulfonylphenoxy and p-hydroxyphenylsulfonylphenoxy. In one aspect of the invention, X may be dialkyl substituted oxazolidinedione, preferably 5,5-dimethyl-2,4-oxazolidinedione.

In another aspect of the invention there is provided a novel pyrroloylacetamide of formula (I'):

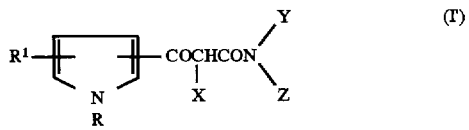

(I')

wherein X may be selected from H, halogen or unsubstituted or substituted acyloxy, sulfonyloxy, aryloxy, heteroaryloxy, arylthio, heteroarylthio, urethane, imido, 2,4-oxazolidinedione, pyridone, pyridazone, phthalimido, succinimido, hydantoinyl, triazole, triazoledione, tetrazole, imidazole, pyrazole and benzotriazole groups;

$R^1$ may be selected from H, halogen, alkyl, aryl, heteroaryl, carboxylic acid, alkoxycarbonyl, aryloxycarbonyl, primary or secondary alkyl- or aryl-amido, alkyl- or aryl- sulfonamido, primary, secondary or tertiary amino, alkoxy, aryloxy, acyloxy, alkyl- or arylcarbamoyl, alkyl- or aryl- sulfamoyl, alkyl- or aryl- sulfonyl and alkyl- or aryl- sulfonyloxy groups.

$R^1$, other than H or halogen, may be substituted with one or more of the same or different substituents of $R^1$ as herein defined.

R, Y and Z may be independently selected from H or unsubstituted or substituted alkyl, aryl or hetero-aryl groups; or Y and Z taken together with the nitrogen atom form a 5–10 membered heterocyclic ring group which may contain one or more further heteroatoms selected from N, O and S, said heterocyclic ring being unsubstituted or substituted.

As used hereinabove the term substituted refers to substitution with one or more of the same or different substituents of $R^1$ as herein defined.

In a preferred aspect the pyrroloylacetamide is a pyrroloylacetanilide, as defined hereinabove for formula (II), specifically a pyrrol-2-oyl or pyrrol-3-oylacetanilide of formula (III) and (IV) hereinabove.

The following are examples of suitable yellow couplers of the invention. (Me is methyl; Et is ethyl; Pr is propyl; Bu is butyl; Ph is phenyl.)

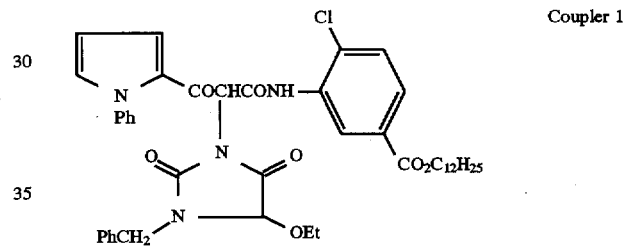

Coupler 1

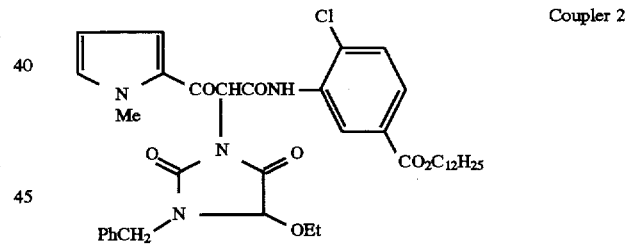

Coupler 2

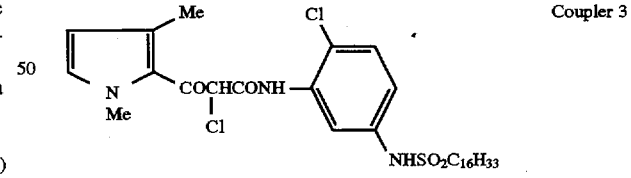

Coupler 3

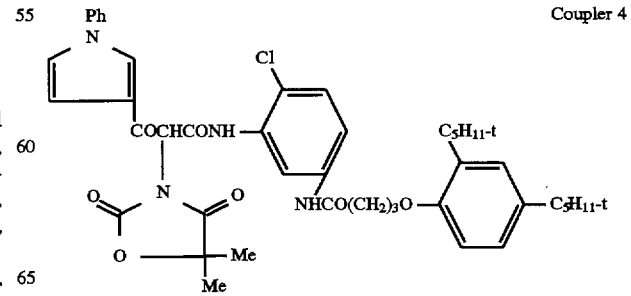

Coupler 4

-continued
Coupler 5
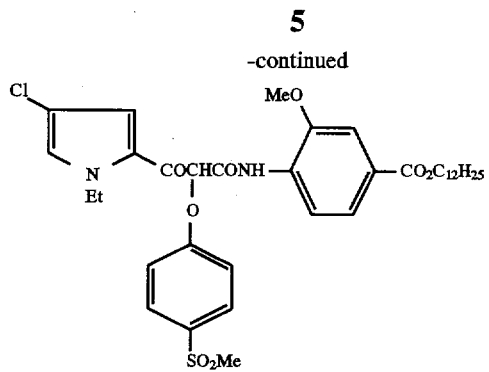
Coupler 6
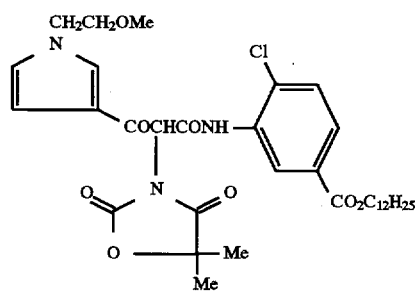
Coupler 7
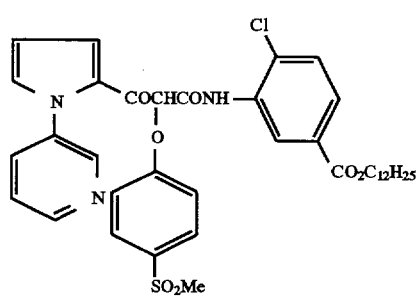
Coupler 8
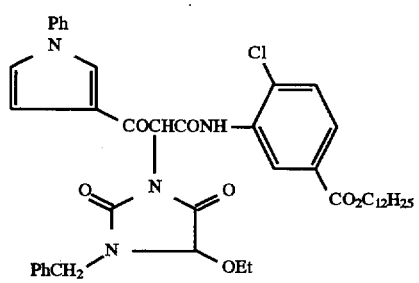
Coupler 9
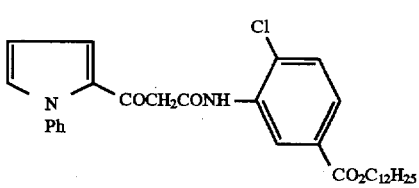
Coupler 10
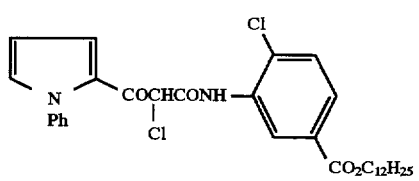
Coupler 11
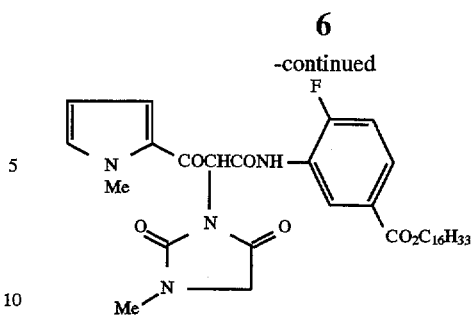
Coupler 12
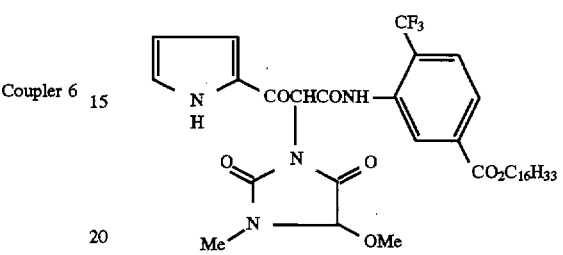
Coupler 13
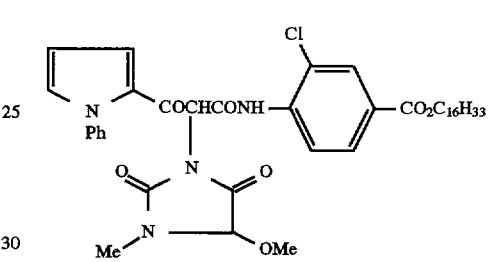
Coupler 14
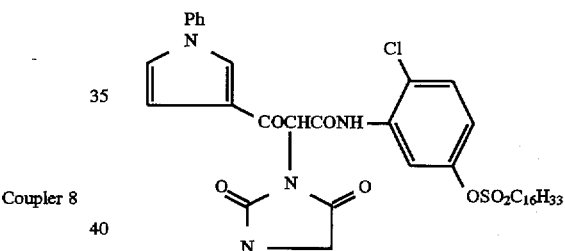
Coupler 15
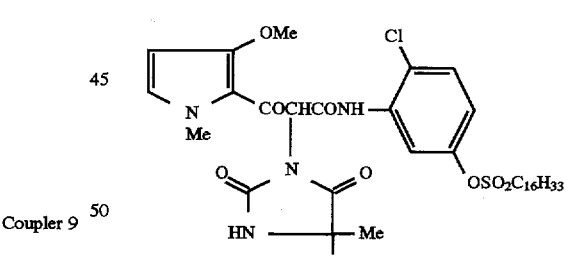
Coupler 16
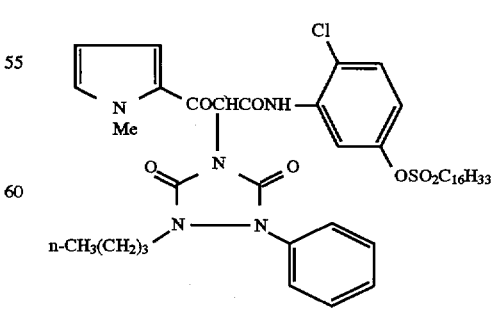

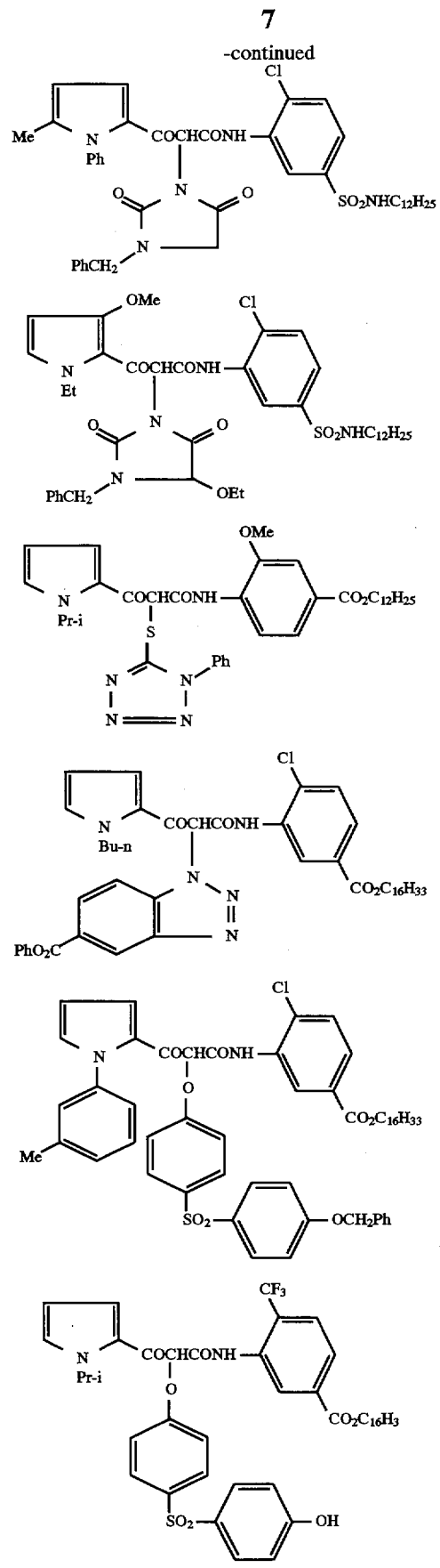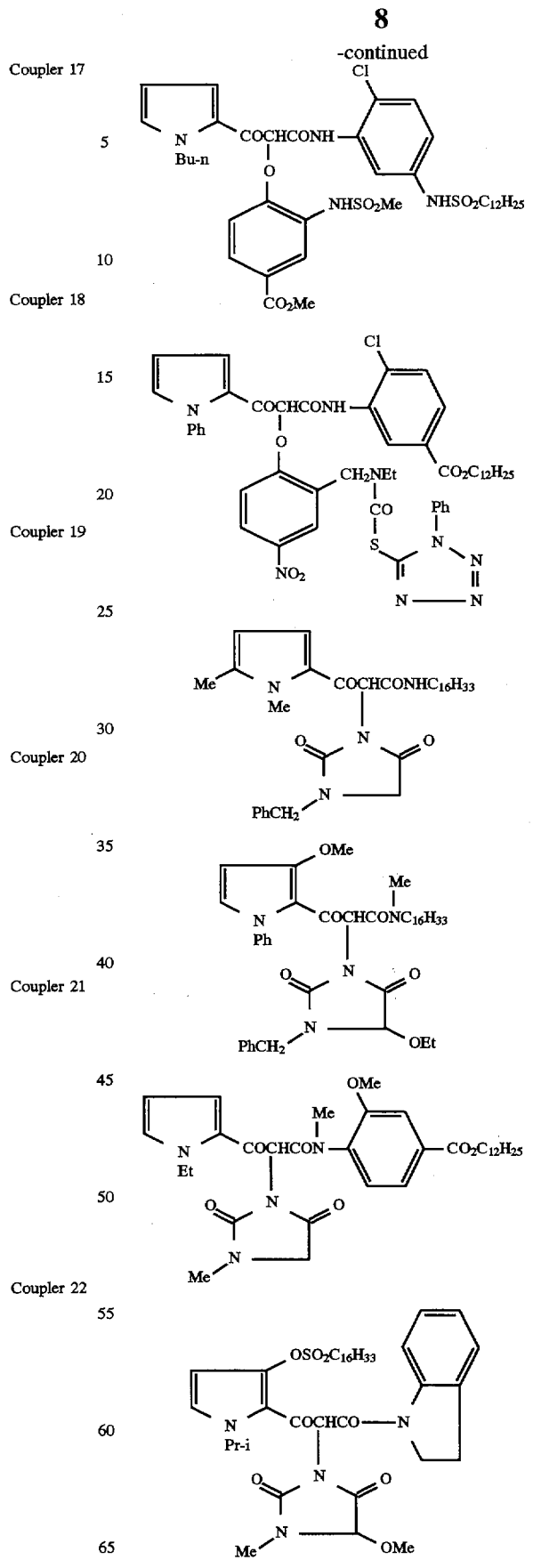

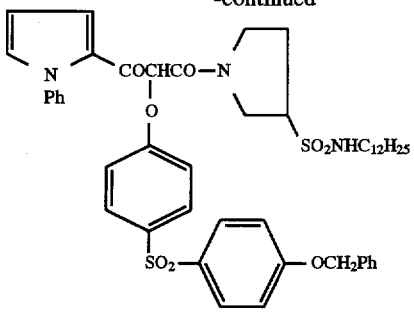

Coupler 29

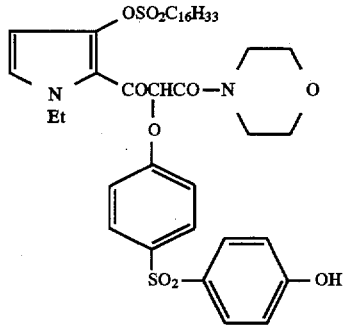

Coupler 30

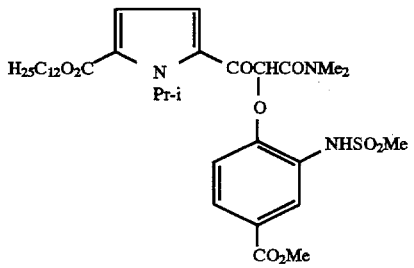

Coupler 31

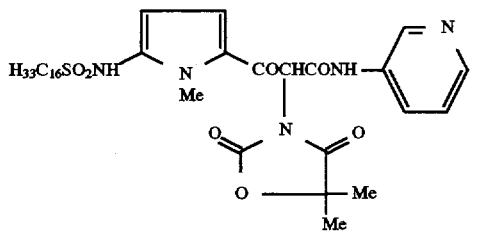

Coupler 32

Unless otherwise specifically stated, "substituents" or substituent groups which may be substituted on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclo-hexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1994, Item 36544, available as described above, which will be identified hereafter by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Scan facilitating is described in Section XIV. Supports, exposure, development systems, and processing methods and agents are described in Sections XV to XX. Certain desirable photographic elements and processing steps, particularly those useful in conjunction with color reflective prints, are described in *Research Disclosure*, Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of a coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl such as oxazolidinyl or hydantoinyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in U.K. Patents and published application Nos. 1,466,728, 1,531,927, 1,533,039, 2,006, 755A and 2,017,704A, the disclosures of which are incorporated herein by reference.

Image dye-forming couplers may be included in the element such as couplers that form cyan dyes upon reaction with oxidized color developing agents which are described in such representative patents and publications as: U.S. Pat. Nos. 2,367,531, 2,423,730, 2,474,293, 2,772,162, 2,895, 826, 3,002,836, 3,034,892, 3,041,236, 4,333,999, 4,883,746 and "Farbkuppler-eine Literature Ubersicht," published in Agfa Mitteilungen, Band III, pp. 156–175 (1961). Preferably such couplers are phenols and naphthols that form cyan dyes on reaction with oxidized color developing agent.

Couplers that form magenta dyes upon reaction with oxidized color developing agent are described in such representative patents and publications as: U.S. Pat. Nos. 2,311,082, 2,343,703, 2,369,489, 2,600,788, 2,908,573, 3,062,653, 3,152,896, 3,519,429, 3,758,309, 4,540,654, and "Farbkuppler-eine Literature Ubersicht," published in Agfa Mitteilungen, Band III, pp. 126–156 (1961). Preferably such couplers are pyrazolones, pyrazolotriazoles, or pyrazolobenzimidazoles that form magenta dyes upon reaction with oxidized color developing agents.

Couplers that form yellow dyes upon reaction with oxidized color developing agent are described in such representative patents and publications as: U.S. Pat. Nos. 2,298,443, 2,407,210, 2,875,057, 3,048,194, 3,265,506, 3,447,928, 4,022,620, 4,443,536, and "Farbkuppler-eine Literature Ubersicht," published in Agfa Mitteilungen, Band III, pp. 112–126 (1961). Such couplers are typically open chain ketomethylene compounds.

Couplers that form colorless products upon reaction with oxidized color developing agent are described in such representative patents as: UK. Patent No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151,343, and 5,234,800.

It may be useful to use a combination of couplers any of which may contain known ballasts or coupling-off groups such as those described in U.S. Pat. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213,490; Japanese Published Application 58-172,647; U.S. Pat. Nos. 2,983,608; 4,070,191; and 4,273,861; German Applications DE 2,706,117 and DE 2,643,965; UK. Patent 1,530,272; and Japanese Application 58-113935. The masking couplers may be shifted or blocked, if desired.

The invention materials may be used in association with materials that accelerate or otherwise modify the processing steps e.g. of bleaching or fixing to improve the quality of the image. Bleach accelerator releasing couplers such as those described in EP 193,389; EP 301,477; U.S. 4,163,669; U.S. Pat. No. 4,865,956; and U.S. Pat. No. 4,923,784, may be useful. Also contemplated is use of the compositions in association with nucleating agents, development accelerators or their precursors (UK Patent 2,097,140; UK. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323.) Also, the compositions may be blocked or coated in protected form as described, for example, in Japanese Application 61/258,249 or U.S. Pat. No. 5,019,492.

The invention materials may further be used in combination with image-modifying compounds such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362,870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

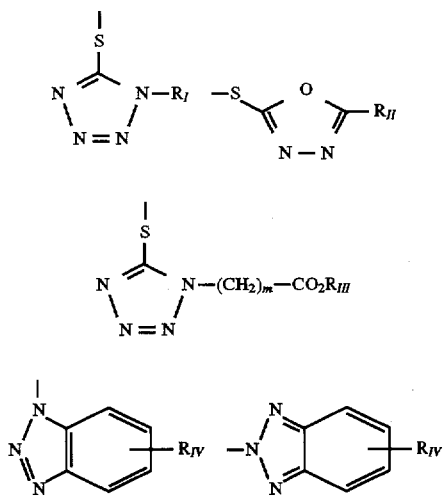

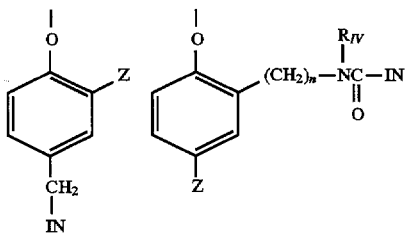

wherein IN is the inhibitor moiety, Z is selected from the group consisting of nitro, cyano, alkylsulfonyl; sulfamoyl (—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group, which produces the time-delayed release of the inhibitor group such as groups utilizing the cleavage reaction of a hemiacetal (U.S. Pat. No. 4,146,396, Japanese Applications 60-249148; 60-249149); groups using an intramolecular nucleophilic substitution reaction (U.S. Pat. No. 4,248,962); groups utilizing an electron transfer reaction along a conjugated system (U.S. Pat. No. 4,409,323; 4,421,845; Japanese Applications 57-188035; 58-98728; 58-209736; 58-209738) groups utilizing ester hydrolysis (German Pat. Application (OLS) No. 2,626,315); groups utilizing the cleavage of imino ketals (U.S. Pat. No. 4,546,073); groups that function as a coupler or reducing agent after the coupler reaction (U.S. Pat. No. 4,438,193; U.S. Pat. No. 4,618,571) and groups that combine the features describe above. It is typical that the timing group or moiety is of one of the formulas:

Suitable developer inhibitor-releasing couplers for use in the present invention include, but are not limited to, the following:

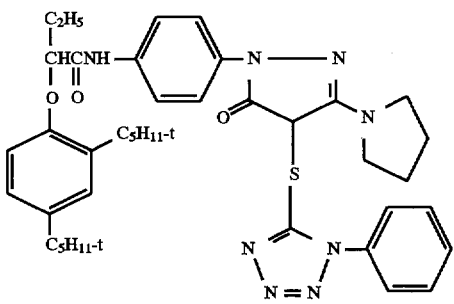

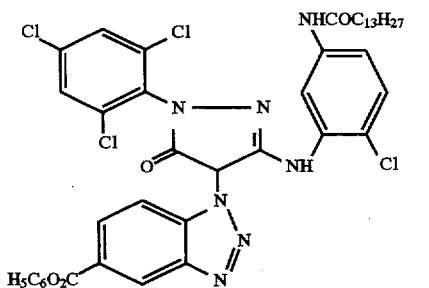

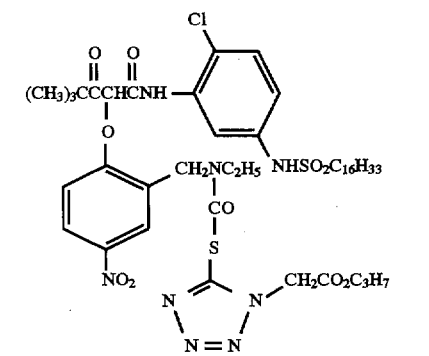

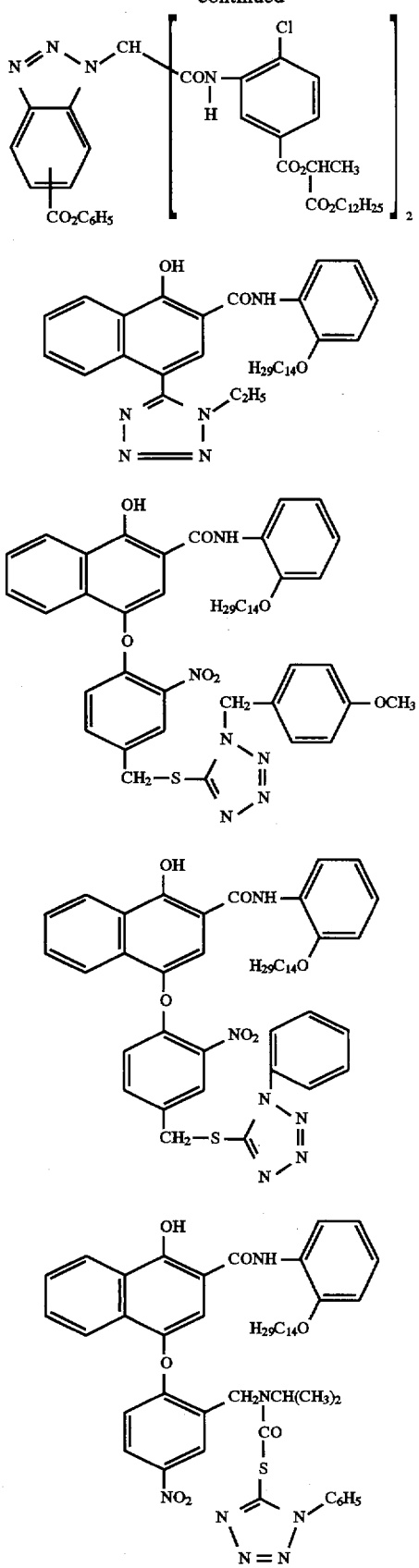
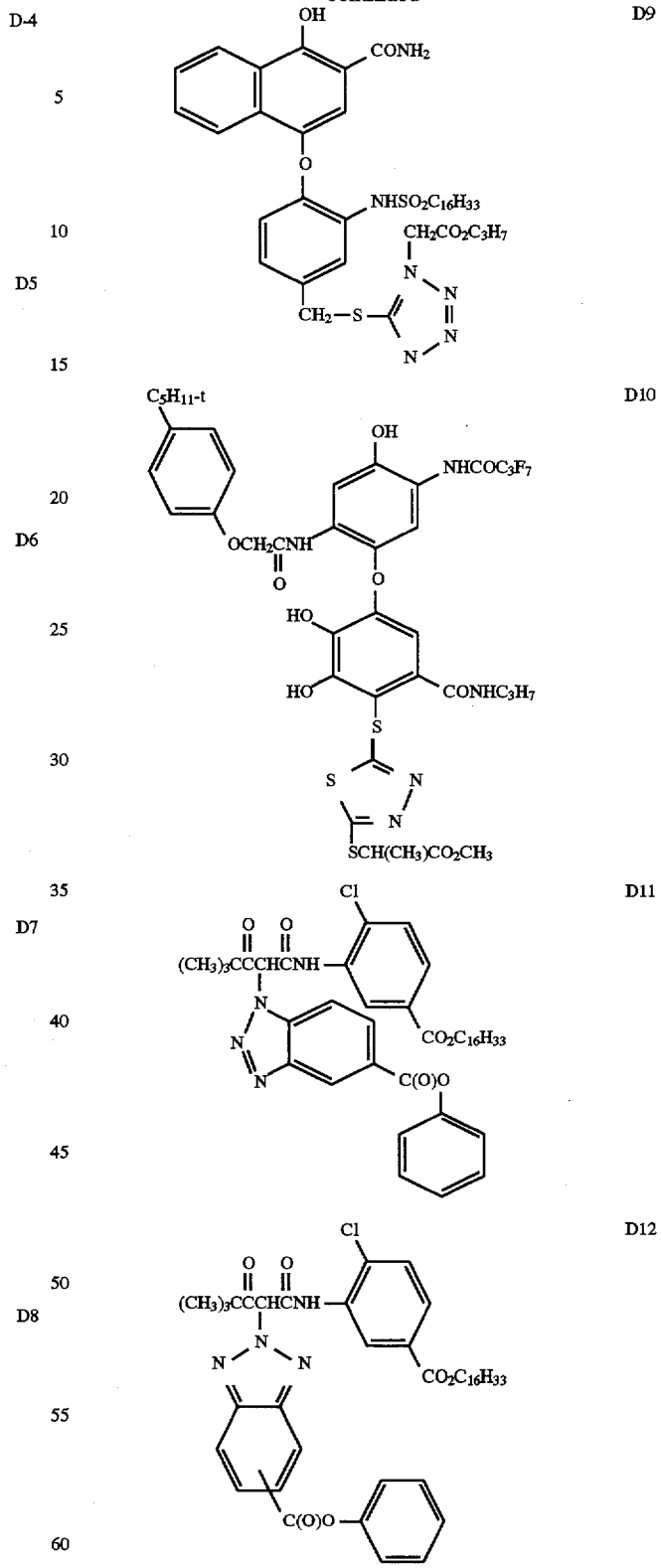
It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference.

Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822; 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T = ECD/t^2$$

where

ECD is the average equivalent circular diameter of the tabular grains in micrometers and t is the average thickness in micrometers of the tabular grains.

The average useful ECD of photographic emulsions can range up to about 10 micrometers, although in practice emulsion ECD's seldom exceed about 4 micrometers. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micrometer) tabular grains. To achieve the lowest levels of granularity it is preferred that aim tabular grain projected areas be satisfied with ultrathin (t<0.06 micrometer) tabular grains. Tabular grain thicknesses typically range down to about 0.02 micrometer. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micrometer. Ultrathin tabular grain high chloride emulsions are disclosed by Maskasky U.S. Pat. No. 5,217,858.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

With negative-working silver halide, the processing step described above provides a negative image. One type of element is designed for image capture. In such an element, speed (the sensitivity of the element to light) is critical to obtaining sufficient image. Such elements may also include masking couplers and other information components since the element is not for direct viewing. These described elements are typically processed in the known Kodak C-41 color process as described in The British Journal of Photography Annual of 1988, pages 191–198. Another type of element is a color print comprising a viewable image on a reflective support. The appearance of the ultimate image rather than the light sensitivity is the major consideration for such an element. Such a print element may be processed in accordance with color print processes such as the RA-4 process of Eastman Kodak Company as described in the British Journal of Photography Annual of 1988, Pp 198–199. Normally, an image capture element of the type first described is optically printed onto a color print element of the second type described.

Such negative working emulsions are typically sold with instructions to process using a color negative method such as the mentioned C-41 or RA-4 process. To provide a positive (or reversal) image, the color development step can be preceded by development with a non-chromogenic developing agent to develop exposed silver halide, but not form dye, and followed by uniformly fogging the element to render unexposed silver halide developable. Such reversal emulsions are typically sold with instructions to process using a color reversal process such as E-6. Alternatively, a direct positive emulsion can be employed to obtain a positive image.

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(2-methanesulfonamido-ethyl)aniline sesquisulfate hydrate, 4-amino-3-methyl-N-ethyl-N-(2-hydroxyethyl)aniline sulfate, 4-amino-3-(2-methanesulfonamido-ethyl)-N,N-diethylaniline hydrochloride and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The yellow coupler in accordance with the invention may be used in combination with other classes of image couplers such as 3-acylamino- and 3-anilino-5-pyrazolones and heterocyclic couplers (e.g. pyrazoloazoles) such as, for example, those described in EP 285,274, U.S. Pat. No. 4,540,654 and EP 119,860; and other 5-pyrazolone couplers containing different ballasts or coupling-off groups such as, for example, those described in U.S. Pat. 4,301,235, U.S. Pat. No. 4,853,319 and U.S. Pat. No. 4,351,897. Yellow or cyan colored couplers (e.g. to adjust levels of interlayer correction) and/or masking couplers such as, for example, those described in EP 213,490, Japanese Published Application 58-172,647, U.S. Pat. No. 2,983,608, German Application DE 2,706, 117C, U.K. Patent 1,530,272, Japanese Application A-113935, U.S. Pat. No. 4,070,191 and German Application DE 2,643,965 may also be used. Said masking couplers may be shifted or blocked.

Synthesis Examples

Following is a description of methods of carrying the present invention into effect.

Couplers 1, 9, and 10 were synthesized by the following sequence starting from 2-acetyl-1-phenylpyrrole.

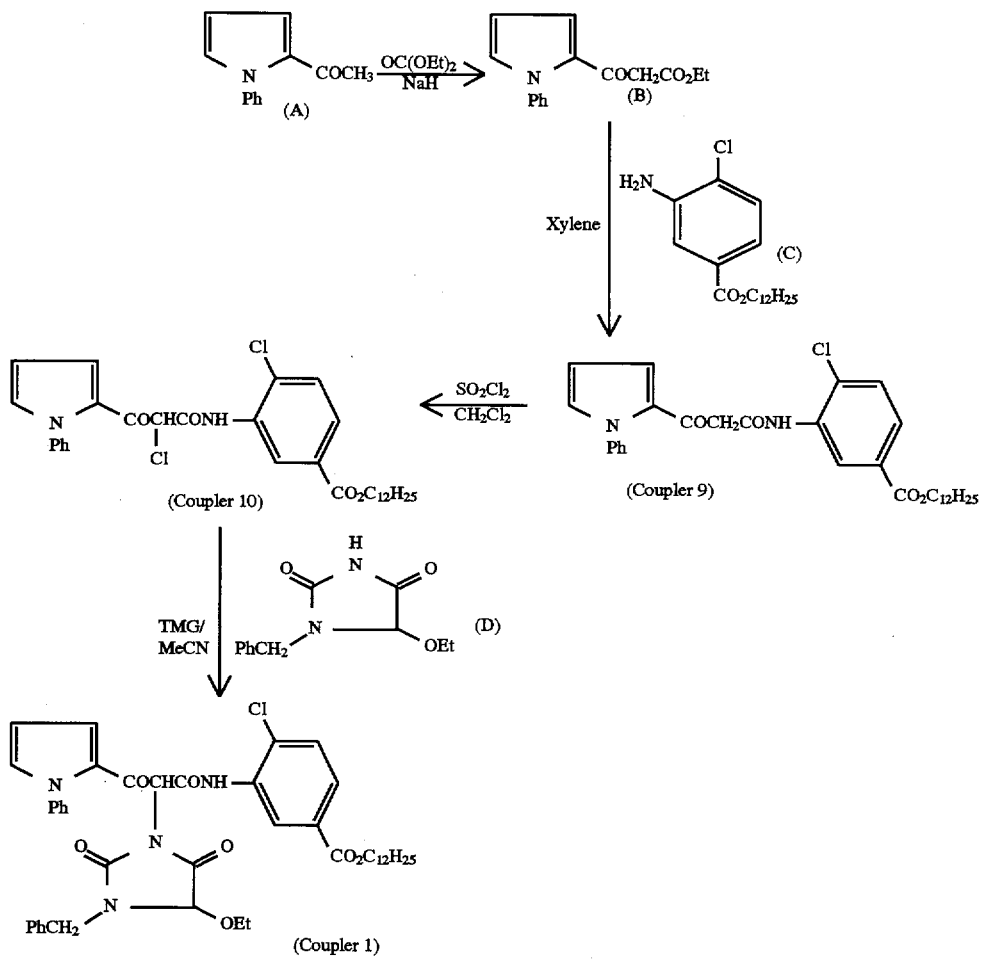

EXAMPLE 1

Synthesis of Coupler 9

1) The Preparation of Intermediate (B)

Sodium hydride (6.0 g of an 80% dispersion in mineral oil, 0.2M) was washed twice with toluene to remove the oil, then it was suspended in diethyl carbonate (14.6 g, 0.123M). The stirred mixture was heated to 70° C. in an oil-bath, then a solution of 2-acetyl-1-phenylpyrrole [Intermediate (A) prepared according to the method given in Zh. Obsch. Khim., 1963, 33, 586–590] (7.4 g, 0.04M) in diethyl carbonate (9.75 g, 0.083M) was added at such a rate as to maintain reflux. During the addition the mixture thickened, so it was heated at 100° C. for 30 minutes before being allowed to cool to room temperature. Glacial acetic acid (7.5 ml) was added followed by ethyl acetate (300 ml) and water (100 ml). The mixture was shaken thoroughly then it was allowed to settle before the organic layer was separated off. The aqueous layer was extracted once more with ethyl acetate (100 ml) and the organic solutions were combined and dried over magnesium sulphate. Removal of the solvent by distillation under reduced pressure afforded a red liquid (9.8 g 96%) which was used without purification in the next stage.

2) The Preparation of Coupler 9

A stirred solution of Intermediate (B) (9.0 g, 0.035M) and the aniline (C) (11.9 g, 0.035M) in xylene (300 ml) was heated under a Dean-Stark head for 20 hours in an oil-bath at 185° C. The solution was allowed to cool to room temperature then the solvent was removed by distillation under reduced pressure. The red residue was triturated with petroleum-ether (bp 60°–80° C.) (100 ml) to afford Coupler 9 as a brown solid which was filtered off, washed with petroleum-ether and dried, 11.8 g (61%).

EXAMPLE 2

Synthesis of Coupler 10

A solution of sulfuryl chloride (2.8 g, 0.021M) in dichloromethane (10 ml) was added over 20 minutes to a stirred solution of Coupler 9 (11.0 g, 0.02M) in dichloromethane (50 ml). The mixture was stirred at room temperature for 2 hours then volatiles were removed by distillation under reduced pressure. The residual brown gum (12.4 g) was triturated with acetonitrile (25 ml) to produce Coupler 10 as a brown solid which was filtered off, washed with acetonitrile and dried, 11.5 g (98%).

EXAMPLE 3

Synthesis of Coupler 1

1,1,3,3-Tetramethylguanidine (4.4 g, 0.039M) was added over 5 minutes to a stirred suspension of Coupler 10 (11.3 g, 0.019M) and the hydantoin (D) (4.7 g, 0.02M) in acetonitrile (90 ml). The mixture was stirred at room temperature for 41 hours then it was added to water (500 ml) which contained concentrated hydrochloric acid (30 ml). This mixture was extracted with ethyl acetate (250 ml), then the extract was back-washed with saturated brine (100 ml) before it was dried over magnesium sulphate. The solvent was removed by distillation under reduced pressure to leave a red viscous liquid (15.3 g). The liquid was purified by column chromatography on 63-200 mesh silica gel, eluting with a 1:9 mixture of ethyl acetate and petroleum-ether (bp 60√–80° C.). Pure Coupler 1 was obtained as a glass, 6.9 g (45%).

EXAMPLE 4

Synthesis of Coupler 8

Coupler 8 was made from 3-acetyl-1-phenylpyrrole (which was obtained as a by-product according to the method described in Zh. Obsch. Khim., 1963,33,586–590) using the same synthetic sequence and reagents and similar procedures to those described for Coupler 1.

EXAMPLE 5

Synthesis of Coupler 2

Coupler 2 was prepared from commercially available 2-acetyl-1-methylpyrrole using the same synthetic sequence and reagents and similar procedures to those described for Coupler 1.

PHOTOGRAPHIC EVALUATION OF YELLOW COUPLERS

The yellow couplers of the present invention (and control compounds) were dispersed in coupler solvent and incorporated into photographic coatings containing a silver bromoiodide emulsion, on a transparent support, according to the following coating diagram:

| Gel Supercoat | Gelatin | 1.50 gm$^{-2}$ |
|---|---|---|
| | Silver bromoiodide | 0.81 gm$^{-2}$ |
| | Coupler | 1.932 mmolm$^{-2}$ |
| Emulsion Layer | Gelatin | 2.42 gm$^{-2}$ |
| | Bis(vinylsulfonyl)methane (hardener) | 0.06 gm$^{-2}$ |
| Support | Cellulose acetate | |

Aqueous dispersions of the couplers were prepared by methods known in the art. The yellow dye-forming coupler dispersions contained 6% by weight of gelatin, 9% by weight of coupler and a 1.0:0.5:1.5 weight ratio of coupler to di-n-butyl phthalate coupler solvent to cyclohexanone auxiliary solvent. The auxiliary solvent was included to aid in dispersion preparation and was removed by washing the dispersion for 6 hours at 4° C. and pH 6.0.

(i) Sensitometric testing

The experimental photographic coatings prepared in this way were slit and chopped into 30 cm×35 mm test strips. After hardening the strips were exposed (1.0 sec) through a 0–4.0 neutral density step wedge (0.2 ND step increments) and Daylight V. Wratten 35±38A filters and 0.3 ND filter then processed through a standard C-41 process as described in the British Journal of Photography Annual (1988) 196–198 using the following steps and process times:

| Developer | 2.5 minutes |
|---|---|
| Bleach | 4.0 minutes |
| Wash | 2.0 minutes |
| Fix | 4.0 minutes |
| Wash | 2.0 minutes |

For each test strip, Status M densities were measured as a function of exposure using a spectral array automatic transmission densitometer. Measurements of sensitometric parameters—minimum density (Dmin), maximum density (Dmax) and contrast ($\gamma$) —were obtained from plots of density vs. log exposure (DlogE curves).

In addition to the above standard conditions, separate strips of each coating were also developed in a competing process employing the same process steps as above but using a developer modified by the addition of 5.0 gl$^{-1}$ citrazinic acid (CZA) and adjusted to pH 10.0 by the addition of sodium carbonate. The ratio of contrast in the competing process to contrast in the standard process ($\gamma_{CZA}/\gamma_{STD}$) is quoted as an indication of in-film reactivity of the coupler.

(ii) Spectrophotometric testing 35 mm Test strips were exposed as above through a 0–0.9 ND step-wedge (0.3 ND increments) and Daylight V, Wratten 35+38A filters and the correct ND filters to give an optical density of about 1.0. The strips were processed using the standard conditions described above and samples cut from the yellow dye image step with density closest to 1.0. Visible absorption spectra of the resultant yellow dyes (normalized to 1.0 density) were obtained using a Pye-Unicam SP8-100 spectrophotometer. Dye hues are expressed in terms of the wavelength corresponding to the maximum absorption peak ($\gamma_{max}$) and the width of the curve at half the peak height—known as the half-bandwidth (HBW).

(iii) Dye stability testing

Yellow dye sample patches of density ca. 1.0 were prepared as for spectrophotometric testing and their absorption spectra measured as above.

Light stability testing: The dye sample patches, protected with a Wratten 2B gelatin filter, are faded for a period of 200 hours accumulated fade using a fadeometer in which the samples are mounted at a fixed distance of 4.0 cm from a pair of 85 W, 6 ft long color matching fluorescent tubes maintained in strictly controlled conditions of 17° C. and 50% relative humidity.

Dark/wet stability testing: The dye sample patches are incubated in a dark oven for a period of 6 weeks accumulated fade at a constant 60° C. and 70% relative humidity.

In both cases the spectrophotometric curves are remeasured after the fade period and the degree of fade quoted as the fractional decrease in density at the wavelength of maximum absorption ($\gamma_{max}$) relative to the initial density prior to fading. Subtle changes in curve shape as the dye fade progresses can be noted.

(iv) Measurement of continued coupling in the bleach

Two sets of 35 mm strips were exposed as in (i) for 1.0 second through a 0–4.0 ND step-wedge (0.2 ND increments) and Daylight V. Wratten 35+38A filters and 0.3 ND filters. One set of strips was processed through a modified C-41 process, in which the pH of the bleach was raised to 5.5 by the addition of 0.880 ammonia, using the following processing sequence:

| Developer | 2.5 minutes |
|---|---|
| Modified Bleach | 4.0 minutes |
| Wash | 2.0 minutes |
| Fix | 4.0 minutes |
| Wash | 2.0 minutes |

The second set of 35 mm test strips was processed through the following sequence, containing the modified bleach (pH5.5) as described above with a stopbath (1% acetic acid solution) and wash step inserted between the developer and bleach steps:

| Developer | 2.5 minutes |
|---|---|
| Stopbath | 1.0 minute |
| Wash | 2.0 minutes |
| Modified Bleach | 4.0 minutes |
| Wash | 2.0 minutes |
| Fix | 4.0 minutes |
| Wash | 2.0 minutes |

For the test strips processed through each of the above sequences, step-wedge densities as a function of exposure were measured using a spectral array automatic transmission densitometer. Measurements of minimum density (Dmin) were obtained from the DlogE curves. The non-imagewise stain due to continued coupling in the bleach ($\Delta$Dmin) was calculated for each coupler by subtracting the Dmin for the test strip processed through the stopbath process from the Dmin for the test strip processed through the process omitting the stopbath step:

$\Delta$Dmin=Dmin (no stopbath process)—Dmin (process with stopbath).

The results of the testing described above are set out in the following Tables 1 and 2:

| Sensitometric Data | | | | | |
|---|---|---|---|---|---|
| COUPLER | Dmin | Dmax | $\gamma$ | $\gamma_{czz}/\gamma$ | CONTINUED COUPLING |
| Control 1 | 0.07 | 1.90 | 1.57 | 0.47 | 0.00 |
| Control 2 | 0.09 | 2.47 | 2.12 | 0.55 | 0.02 |
| Control 3 | 0.11 | 2.72 | 2.38 | 0.68 | 0.07 |
| Coupler 1 | 0.09 | 2.42 | 2.10 | 0.62 | 0.02 |
| Coupler 8 | 0.09 | 2.41 | 2.17 | 0.63 | 0.01 |
| Coupler 2 | 0.08 | 2.25 | 1.95 | 0.61 | 0.00 |

| Spectrophotometric and Dye Fade Data | | | | |
|---|---|---|---|---|
| COUPLER | $\gamma$ max (nm) | HBW (nM) | % Light Fade | % Dark/wet Fade |
| Control 1 | 448.5 | 88 | −0.02 | −0.05 |
| Control 2 | 446.0 | 92.5 | −0.12 | −0.18 |
| Control 3 | 450.0 | 88.5 | −0.20 | −0.12 |
| Coupler 1 | 450.5 | 88 | −0.12 | −0.17 |
| Coupler 2 | 448.5 | 85 | −0.06 | −0.13 |

Couplers 1 to 32 have the structures described above. The chemical structures of Controls 1, 2 and 3 are as follows:

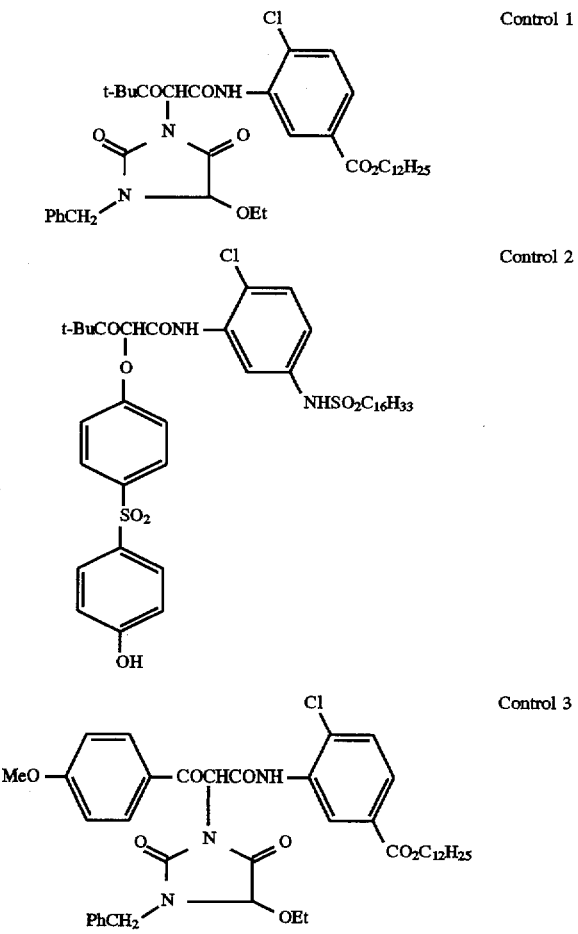

From the above, it will be seen that the yellow couplers, in accordance with the present invention as hereinbefore described, have properties which are comparable with the control couplers which are used in commercially available photographic materials. In particular, Couplers 1 and 2 appear to provide a balance of properties that can be employed as is or with suitable addenda to achieve further improvement.

The entire contents of the various patent applications, patents and other publications referred to in this specification are incorporated herein by reference.

What is claimed is:

1. A photographic element comprising a silver halide emulsion layer having associated therewith a dye-forming coupler of formula (I):

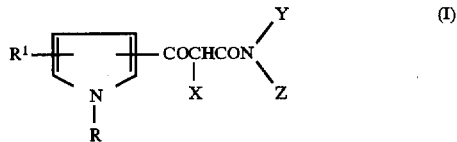

wherein X is H or a coupling-off group, R and $R^1$ are independently selected from H and substituent groups; Y and Z are independently selected from H and alkyl, aryl or heteroaryl groups; provided that Y and Z taken together with the nitrogen atom may form a 5–10 membered heterocyclic ring group which may contain one or more further heteroatoms selected from N, O and S.

2. The element as claimed in claim 1 wherein the dye-forming coupler is a yellow dye-forming pyrroloylacetanilide of formula (II):

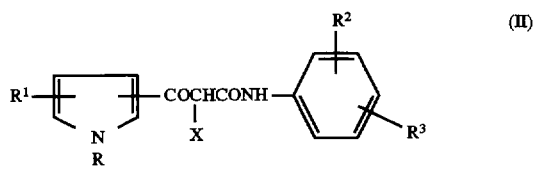

wherein X is H or a coupling-off group; and R, $R^1$, $R^2$, and $R^3$ are independently selected from H and substituent groups.

3. A photographic element as claimed in claim 2 wherein the coupler is represented by formula (III):

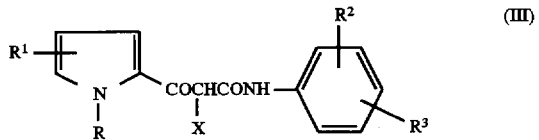

wherein X is H or a coupling-off group; and R, $R^1$, $R^2$, and $R^3$ are independently selected from H and substituent groups.

4. The element of claim 3 in which the coupler is a pyrrol-2-oylacetanilide and R is methyl or phenyl.

5. A photographic element as claimed in claim 2 wherein coupler is represented by formula (IV):

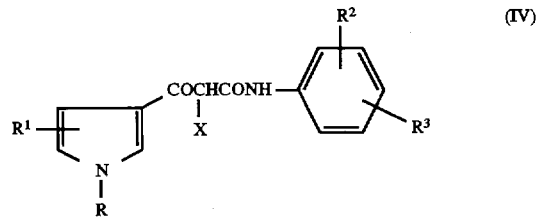

wherein X is H or a coupling-off group; and R, $R^1$, $R^2$, and $R^3$ are independently selected from H and substituent groups.

6. The element of claim 2 wherein $R_2$ is selected from halogen, alkoxy and trifluoromethyl groups.

7. The element of claim 1 wherein at least one of R, $R^1$, $R^2$, and $R^3$ are selected, independently, from H, coupler-solubilizing groups, ballasting groups and dye hue-modifying groups.

8. The element of claim 1 in which R is selected from the group consisting of hydrogen, alkyl, aryl and heteroaryl groups.

9. The element of claim 8 in R is selected from an alkyl group of up to 8 carbon atoms, a phenyl group and a pyridinyl group.

10. The element of claim 1 in which $R^1$, $R^2$, and $R^3$ are independently selected from the group consisting of H, halogen, alkyl, aryl, heteroaryl, carboxylic acid, alkoxycarbonyl, aryloxycarbonyl, amido, sulfonamido, amino, alkoxy, aryloxy, acyloxy, carbamoyl, sulfamoyl, sulfonyl and sulfonyloxy groups.

11. The element of claim 1 wherein at least one of $R^1$, $R^2$, and $R^3$ contains at least six carbon atoms.

12. The element of claim 1 wherein $R_1$ is selected from H, halogen, alkyl, alkoxy, alkylsulfonyloxy, alkylsulfonamido and alkoxycarbonyl groups.

13. The element of claim 1 wherein the coupler has one of the formulas:

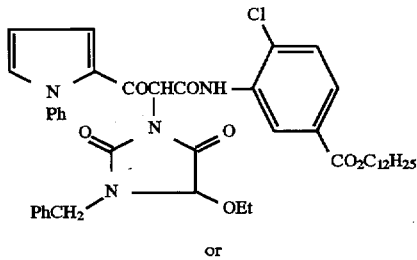

or

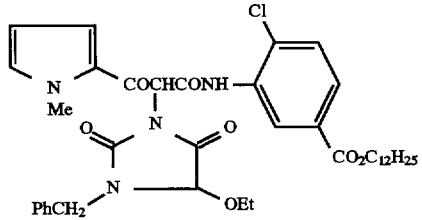

14. A method of forming an image in an element as described in claim 1 after the same has been exposed to light, comprising contacting the element with a color developing agent.

* * * * *